(12) United States Patent
Lacey

(10) Patent No.: US 7,573,976 B2
(45) Date of Patent: Aug. 11, 2009

(54) COMPUTED TOMOGRAPHY SYSTEM AND APPARATUS

(75) Inventor: Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/852,374

(22) Filed: Sep. 10, 2007

(65) Prior Publication Data

US 2009/0067571 A1    Mar. 12, 2009

(51) Int. Cl.
*G01N 23/00* (2006.01)
(52) U.S. Cl. ......................................... 378/19; 378/147
(58) Field of Classification Search .................. 378/19, 378/147, 149, 154
See application file for complete search history.

(56) References Cited

U.S. PATENT DOCUMENTS

2006/0233298 A1* 10/2006 Igarashi et al. ................. 378/19
2007/0133737 A1*  6/2007 Yahata et al. .................. 378/19

* cited by examiner

*Primary Examiner*—Jurie Yun

(57) ABSTRACT

A computed tomography system is disclosed herein. The computed tomography system includes a rotatable gantry portion and an x-ray source mounted to the rotatable gantry portion. The computed tomography system also includes a detector assembly mounted to the rotatable gantry portion and positioned to receive an x-ray beam from the x-ray source. The detector assembly includes a plurality of x-ray attenuating collimation plates with a generally x-ray translucent stiffening member attached to one or more of the plurality of x-ray attenuating collimation plates.

7 Claims, 5 Drawing Sheets

COMPUTED TOMOGRAPHY SYSTEM AND APPARATUS

FIELD OF THE INVENTION

This disclosure relates generally to a computed tomography system and apparatus involving a stiffening member attached to one or more x-ray attenuating collimation plates.

BACKGROUND OF THE INVENTION

Typically, in computed tomography (CT) imaging systems, an x-ray source emits a fan-shaped x-ray beam toward a subject or object, such as a patient or a piece of luggage, positioned on a support. The beam, after being attenuated by the subject, impinges upon a detector assembly. The intensity of the attenuated x-ray beam received at the detector assembly is typically dependent upon the attenuation of the x-ray beam by the subject. Each detector element of the detector assembly produces a separate electrical signal indicative of the attenuated x-ray beam received.

In known third generation CT systems, the x-ray source and the detector assembly are rotated on a rotatable gantry portion around the object to be imaged so that a gantry angle at which the fan-shaped x-ray beam intersects the object constantly changes. Data representing the strength of the received x-ray beam at each of the detector elements is collected across a range of gantry angles. The data are ultimately processed to form an image of the object.

It is commonly known that a percentage of the photons in the x-ray beam will interact with the subject or the support and that the interaction will result in the generation of secondary x-ray photons. Collectively, these secondary x-ray photons are commonly referred to as scattered x-ray photons. It is well-known that scattered x-ray photons travel in directions that are not predictable and may be a source of noise in the image. Since the x-ray photons are a source of noise, they need to be effectively managed before reaching the detector elements in order to maintain an acceptable signal-to-noise-ratio.

In known third generation CT scanners, the effects of scattered x-ray photons are managed through a post patient collimator. The post patient collimator is mounted on the detector assembly and it is located in a position between the subject and the detector elements. Typically the post patient collimator includes a plurality of thin collimation plates comprising a highly x-ray attenuating material such as tungsten, lead, molybdenum, etc. that are focally aligned to a focal spot of the x-ray source. Most scattered x-ray photons travel along paths that are not focally aligned to the focal spot of the x-ray source and, therefore, the scattered x-ray photons are effectively blocked by the highly x-ray attenuating material in the collimation plates. The post patient collimator is also used to control off-focus x-ray photons. For the purposes of this disclosure, off-focus x-ray photons are defined to include x-ray photons that originate from the x-ray source, but do not pass through the focal spot. The post patient collimator is designed to block both off-focus x-ray photons and scattered x-ray photons.

In order for the post patient collimator to perform acceptably well, it is critical that the thin collimation plates remain accurately aligned to the focal spot of the x-ray source. If the collimation plates are not accurately aligned, they may allow some of the off-focus x-ray photons or the scattered x-ray photons to impinge upon the detector elements. It is well-known that either off-focus x-ray photons or scattered x-ray photons contacting the detector elements will result in a lower signal-to-noise ratio, which causes a degradation in image quality.

For known third generation CT systems, a fast gantry rotation speed is necessary to obtain high temporal resolution in the image. However, as the gantry rotation speed increases, the collimation plates are subjected to a significantly larger deflecting force. Since the rotatable gantry portion is rotating, the deflecting force acting on each collimation plate increases as the square of the gantry rotation speed. Because of this relationship, even a small increase in the gantry rotation speed leads to a significantly higher force acting to deflect each of the collimation plates. The problem is that faster gantry rotation speeds can lead to significant deflection of the collimation plates, allowing more off-focus x-ray photons and scattered photons to contact the detector elements, which ultimately causes a degradation in image quality.

A known solution is to brace the collimation plates with tungsten wires in an x-direction of the detector assembly. Since tungsten is highly x-ray attenuating, the tungsten wires absorb some of the x-ray photons that have not been scattered before they reach the detector elements. Using tungsten wires to brace the collimation plates may not be desirable since the tungsten wires blocks x-ray photons that would otherwise be used to create a higher quality image for a given x-ray dose. In addition to absorbing x-ray photons, the tungsten wires may also demark where x-rays may pass, which can induce image artifacts.

BRIEF DESCRIPTION OF THE INVENTION

The above-mentioned shortcomings, disadvantages and problems are addressed herein which will be understood by reading and understanding the following specification.

In an embodiment, a computed tomography system includes a rotatable gantry portion and an x-ray source mounted to the rotatable gantry portion. The computed tomography system also includes a detector assembly mounted to the rotatable gantry portion and positioned to receive an x-ray beam from the x-ray source. The detector assembly includes a plurality of x-ray attenuating collimation plates with a stiffening member attached to one or more of the plurality of x-ray attenuating collimation plates. The stiffening member is made from a generally x-ray translucent material.

In another embodiment, a computed tomography system includes a rotatable gantry portion and an x-ray source mounted on the rotatable gantry portion. A detector assembly is mounted generally opposite the x-ray source. The detector assembly includes a plurality of x-ray attenuating collimation plates configured to block a scattered x-ray photon. The detector assembly also includes a carbon composite stiffening member attached to one or more of the plurality of x-ray attenuating collimation plates.

In another embodiment, a detector assembly includes a plurality of generally arc-shaped rails that are generally parallel to each other and a plurality of x-ray attenuating collimation plates positioned between the generally arc-shaped rails. The detector assembly also includes a stiffening member attached to one or more of the plurality of x-ray attenuating collimation plates and to the generally arc-shaped rails. The stiffening member is selected from the group consisting of carbon composite, carbon fiber reinforced plastic, ceramic and aluminum.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
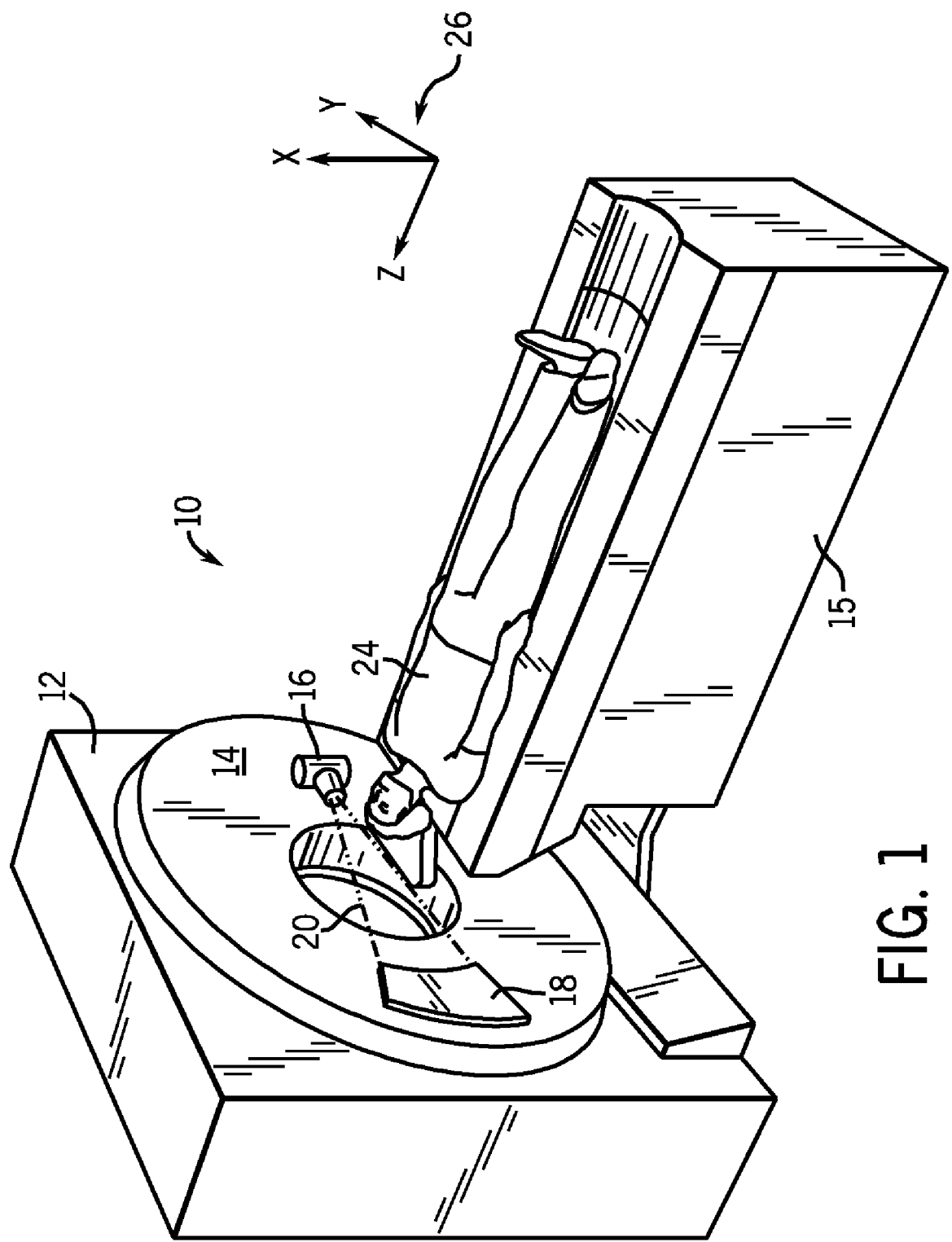
FIG. 1 is a schematic diagram illustrating a computed tomography system in accordance with an embodiment.

Referring to FIG. 1, a schematic representation of a computed tomography (CT) system 10 according to an embodiment is shown. The CT system 10 includes a gantry 12, a rotatable gantry portion 14, and a support 15. The rotatable gantry portion 14 is adapted to retain an x-ray source 16 and a detector assembly 18. The x-ray source 16 is configured to emit an x-ray beam 20 towards the detector assembly 18. The support 15 is configured to support a subject 24 being scanned. Hereinafter, the terms "subject" and "object" shall include anything capable of being imaged. The support 15 is capable of translating the subject 24 along a z-direction with respect to the gantry 12 as indicated by coordinate axis 26.

Figure 2:
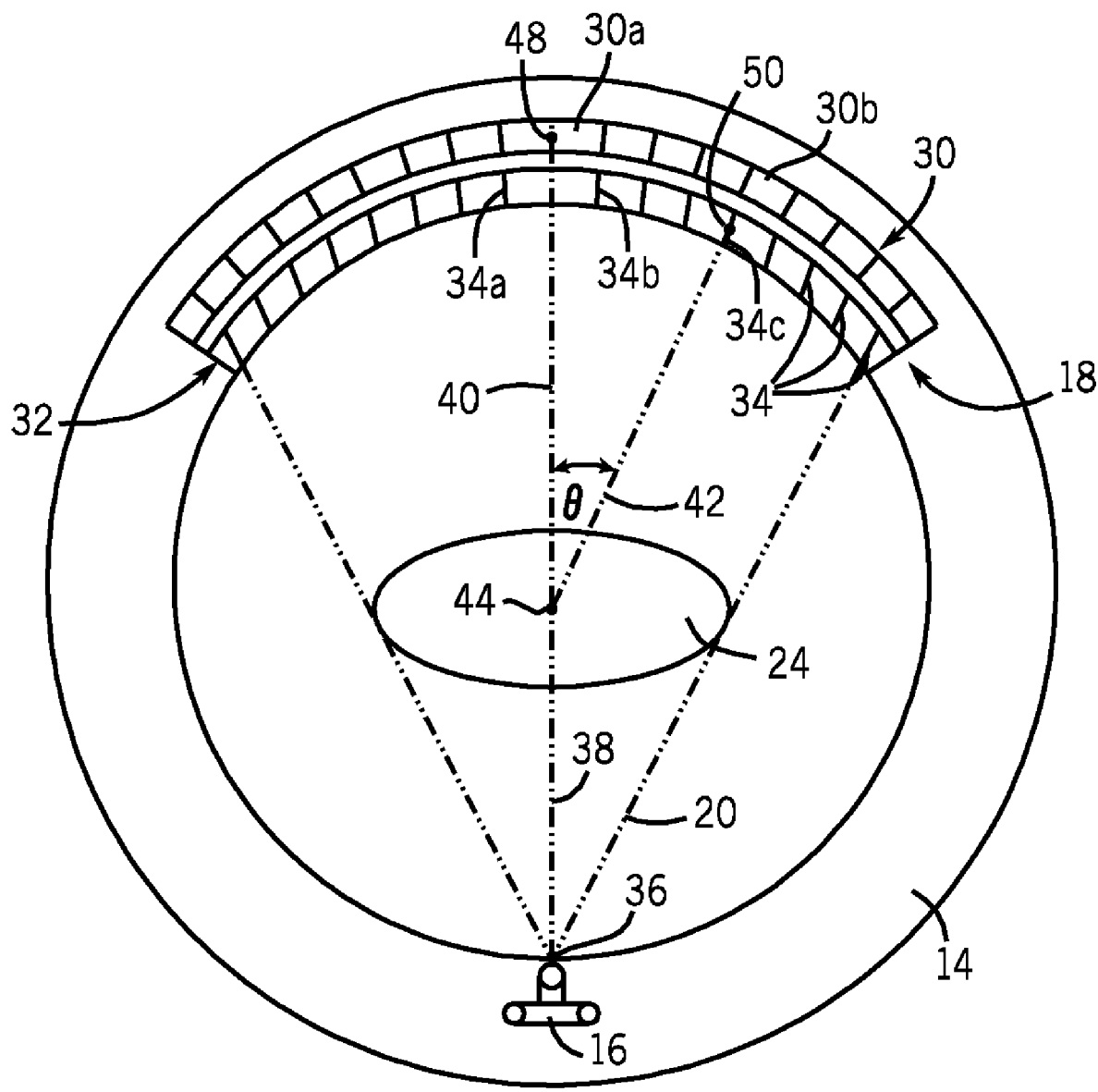
FIG. 2 is a schematic diagram illustrating a rotatable gantry portion of the computed tomography system of FIG. 1.

Referring to FIG. 2, a more detailed schematic representation is shown of the rotatable gantry portion 14 according to an embodiment. The x-ray source 16 and the detector assembly 18 are disposed on the rotatable gantry portion 14. The detector assembly 18 includes a plurality of detector elements 30 and a post patient collimator 32.

The x-ray source 16 emits a fan-shaped x-ray beam 20 from a focal spot 36. The x-ray beam 20 includes a plurality of x-ray photons (not shown) configured to pass through the subject 24 being scanned. After passing through the subject 24, the x-ray beam 20 travels through the post patient collimator 32. The post patient collimator 32 is configured to minimize image quality degradation caused by off-focus x-ray photons (not shown) and scattered x-ray photons (not shown). For the purposes of this disclosure, the term "scattered x-ray photon" should be defined to include x-ray photons that are emitted from the subject 24 or the support 15 (shown in FIG. 1).

The post patient collimator 32 is disposed between the subject 24 being scanned and the plurality of detector elements 30. The post patient collimator 32 includes a plurality of x-ray attenuating collimation plates 34, comprising a highly x-ray attenuating material such as tungsten, lead, molybdenum, etc. Each x-ray attenuating collimation plate 34 is thin and generally aligned to the focal spot 36 of x-ray source 16.

The post patient collimator 32 is configured to minimize the effect of scattered x-ray photons (not shown) and off-focus x-ray photons (not shown). A line segment 38 combined with a line segment 40 form a straight line and show the path of an x-ray photon (not shown) that originates from the x-ray source 16. In comparison a line segment 42 represents the path of a scattered x-ray photon resulting from an interaction of the x-ray photon that traveled along the path represented by line segment 38 with the subject at a point 44. The path of the scattered photon represented by the line segment 42 differs from the path of the photon that interacts with the subject 24 at the point 44 by an angle θ.

The general alignment of the collimation plates 34 to the focal spot 36 allows the x-ray photons (not shown) that originate generally from the focal spot 36 to pass between the collimation plates 34 so that they can be detected by the plurality of detector elements 30. The path of an x-ray photon that originates generally from the focal spot 36 is schematically represented by the combination of the line segment 38 and the line segment 40. The x-ray photon whose path is represented by the combination of the line segment 38 and the line segment 40 passes between a collimation plate 34a and a collimation plate 34b before contacting a detector element 30a at a point 48. In comparison, the scattered x-ray photon (not shown), whose path is represented by the line segment 42, arrives at the post patient collimator 32 along a path that does not align with the focal spot 36 of the x-ray source 16. As a result, the scattered x-ray photon contacts a collimation plate 34c at a point 50. Since the plurality of collimation plates 34 are made of a highly x-ray attenuating material, the scattered x-ray photon is absorbed by the collimation plate 34c before reaching the plurality of detector elements 30. Without the post patient collimator 32, the scattered x-ray photon would have been detected at detector element 30b, where it would have been a source of unwanted noise and resulted in lower image quality.

As the rotatable gantry portion 14 is rotating, a force vector from the rotation acts in an outward radial direction from the center of rotation. The collimation plates 34 are generally aligned to the focal spot 36 of the x-ray source 16. Since the collimation plates 34 are not aligned with the direction of the centrifugal force, the centrifugal force acts to bend or deflect the collimation plates 34 during the acquisition of image data.

If the collimation plates 34 bend or deflect, they can cause multiple problems. The deflected collimation plates 34 will not be as effective at blocking off-focus x-ray photons (not shown) and scattered x-ray photons (not shown). For example, the line segment 42 represents the path of a scattered x-ray photon. If the collimation plate 34c were to deflect enough, it would not block the scattered x-ray photon and the scattered x-ray photon would contact detector element 30b. Each scattered x-ray photon that passes through the post patient collimator 32 may result in lower image quality. Alternatively, if the collimation plates 34 deflect significantly, they are also more likely to reject x-ray photons that originate generally from the focal spot 36. This can also lead to diminished image quality.

Figure 3:
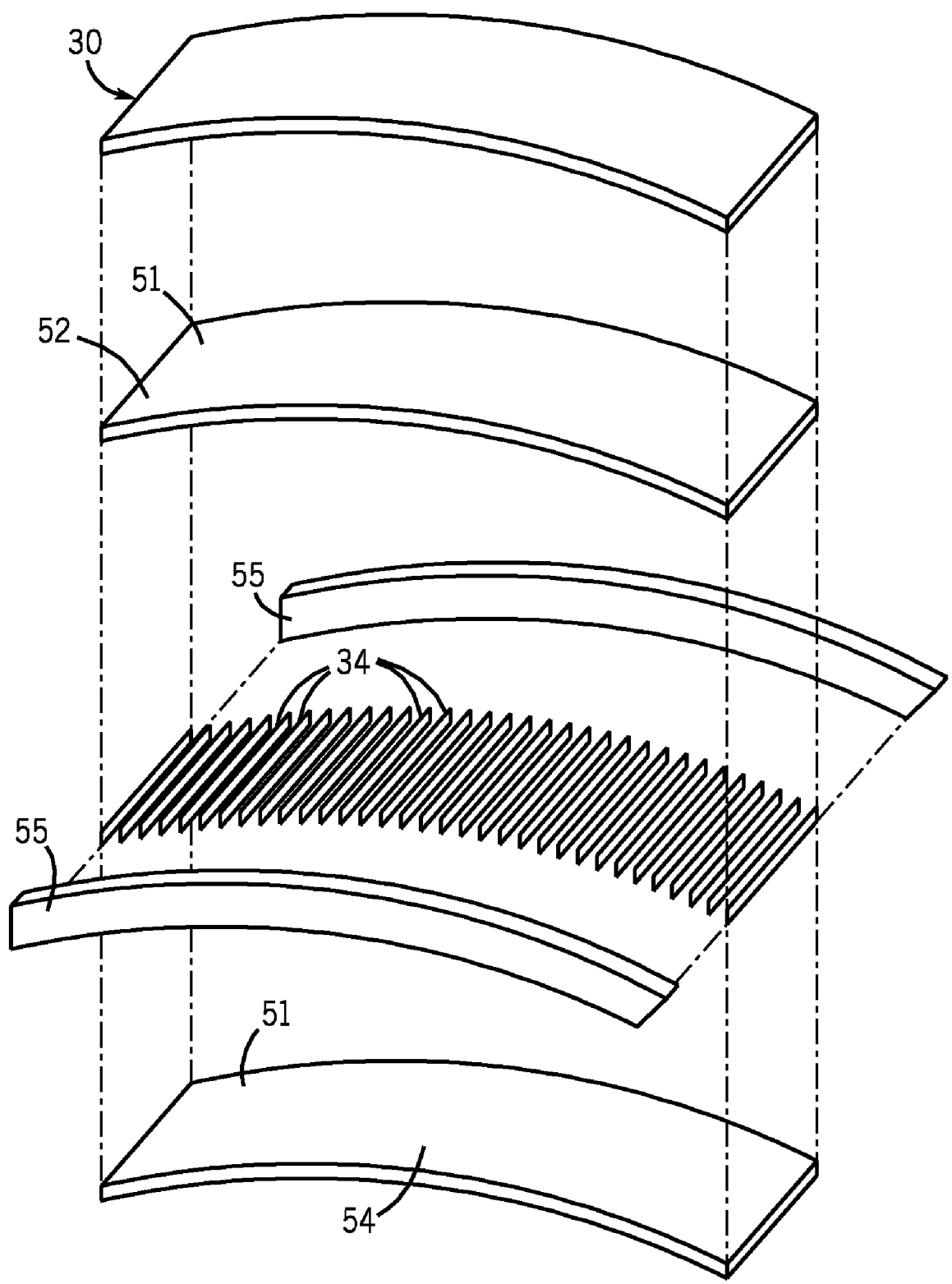
FIG. 3 is a detailed exploded view of a detector assembly in accordance with an embodiment.
Figure 4:
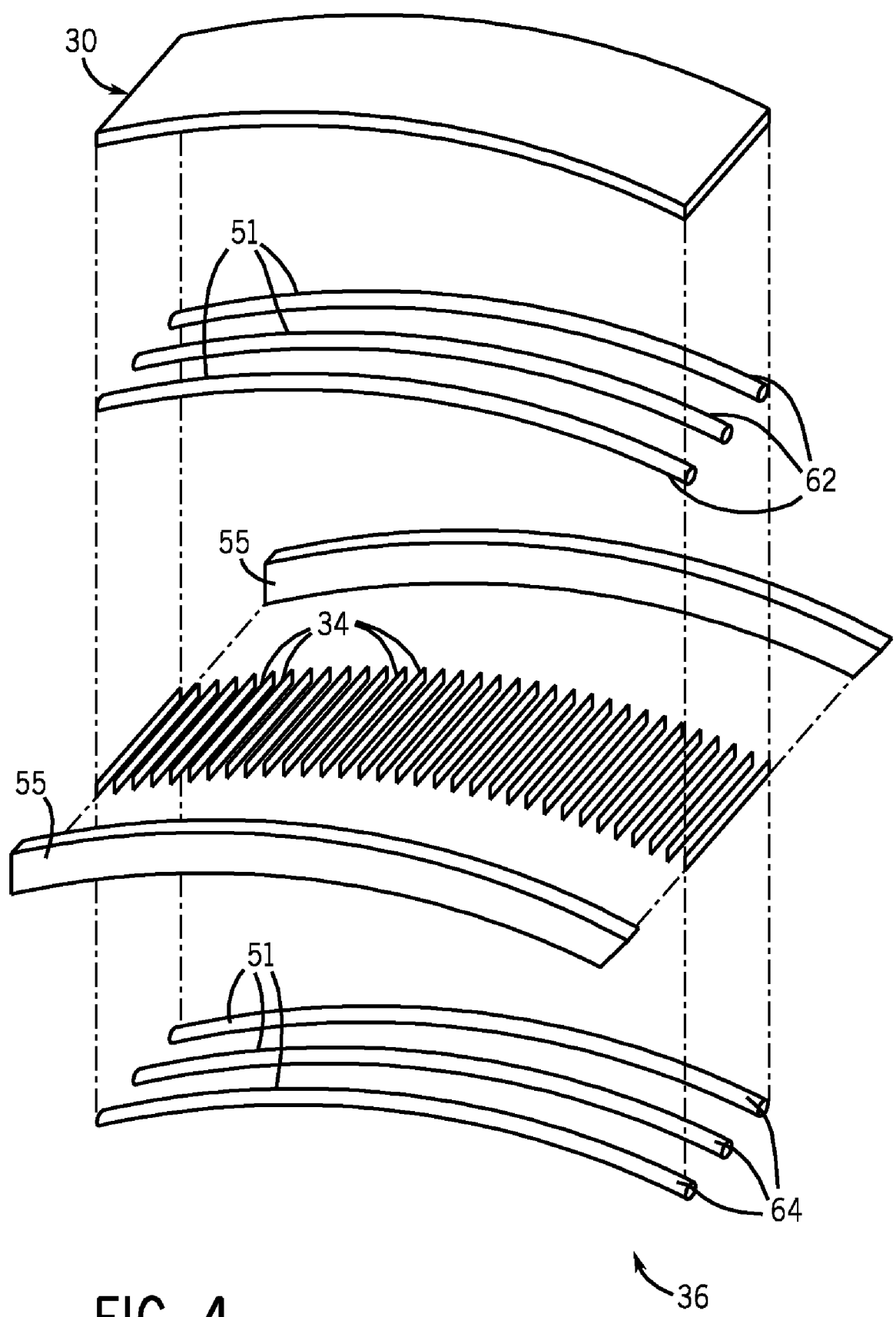
FIG. 4 is a detailed exploded view of a detector assembly in accordance with another embodiment.
Figure 5:
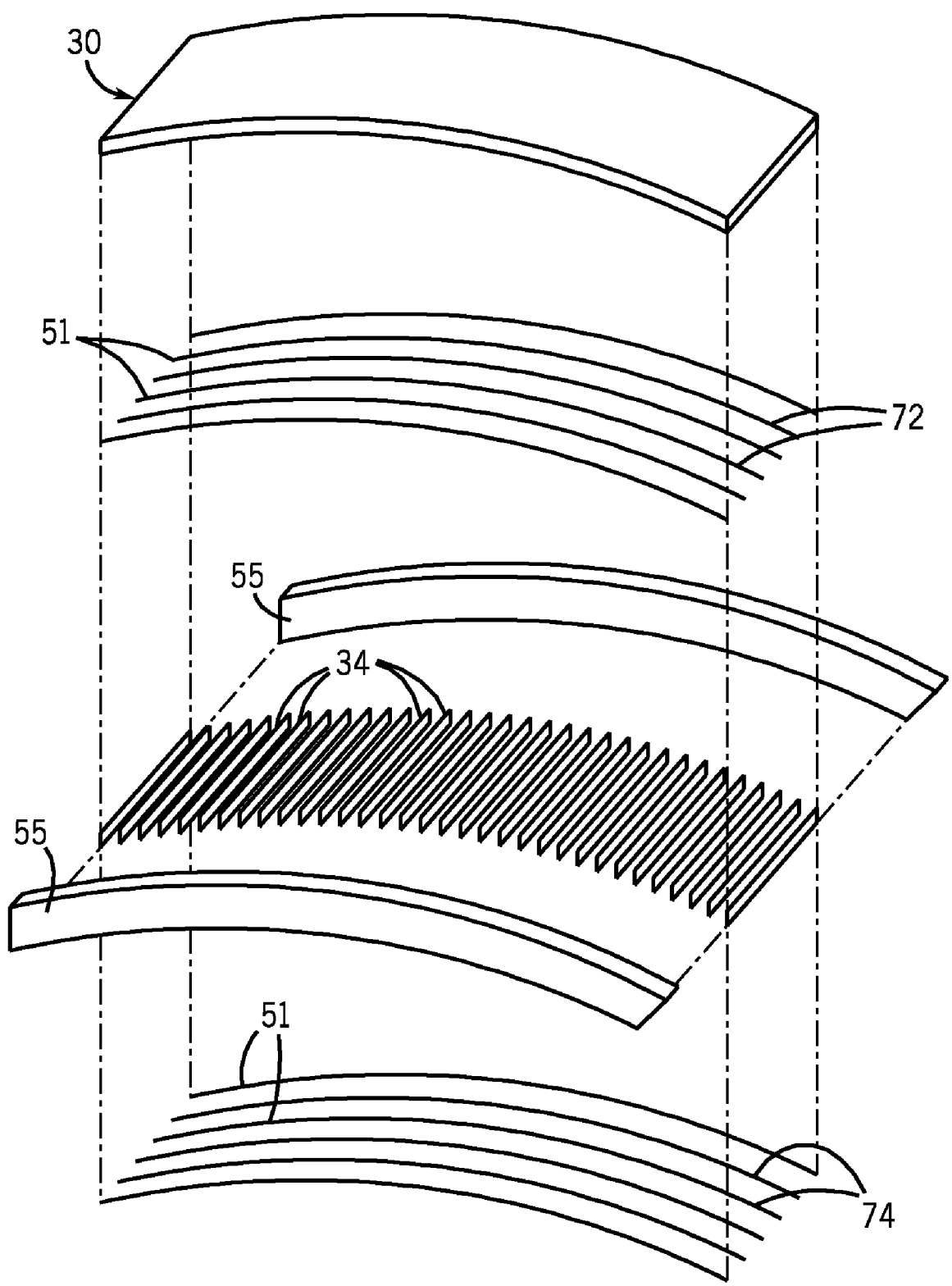
FIG. 5 is a detailed exploded view of the detector assembly in accordance with yet another embodiment.

One method of minimizing the effects of deflection and bending of the collimation plates 34 on image quality is to attach a stiffening member 51 (shown in FIG. 3) to the collimation plates 34. FIGS. 3, 4, and 5 will be used to schematically illustrate various embodiments using the stiffening member 51 to keep the collimation plates 34 properly aligned in order to maintain good image quality.

Referring to FIG. 3, a schematic representation of a detailed exploded view of the detector assembly 36 is shown in accordance with an embodiment. The detector assembly 36 includes a radially outer stiffening plate 52, a radially inner stiffening plate 54 and a pair of rails 55. The plurality of collimation plates 34 and the plurality of detector elements 30 are attached to the pair of rails 55. The outer stiffening plate 52 and the inner stiffening plate 54 are configured for attachment to the plurality of collimation plates 34. The outer stiffening plate 52 is disposed between the plurality of detector elements 30 and the collimation plates 34 while the inner stiffening plate 54 is attached to the collimation plates 34 on the side opposite from the detector elements 30. According to another embodiment, only one of the outer stiffening plate 52 and the inner stiffening plate 54 could be attached to the plurality of collimation plates 34.

For all of the embodiments incorporating a stiffening plate 52, 54 as a stiffening member, it should be understood that the stiffening plate does not need to comprise smooth parallel surfaces as shown in FIG. 3. Embodiments where either the outer stiffening plate 52 or the inner stiffening plate 54 have grooves or recesses causing the stiffening plate 52, 54 to vary in thickness can be envisioned. Additionally, for the embodiments involving the stiffening plate 52, 54 as the stiffening member 51, it should be understood that the outer stiffening plate 52 or the inner stiffening plate 54 may be attached to the rail 55 to further enhance the stiffness. Optionally, it may be possible to fabricate the rails 55 and the outer stiffening plate 52 and/or the rails 55 and the inner stiffening plate 54 as one integral piece.

Referring to FIG. 4, according to another embodiment, the stiffening members 51 may comprise one of more stiffening spars 62, 64. While the embodiment in FIG. 4 is shown having three radially outer stiffening spars 62 and three radially inner stiffening spars 64, it should be appreciated that any number of stiffening spars 62, 64 may be disposed in contact with the collimation plates 34. Additionally, the stiffening spars can be made with any cross section. A partial list of acceptable cross sections for the stiffening spars 62, 64 includes generally rectangular, generally circular, generally oval, and shaped like the letter "I", as would typically be found on an I-beam used for construction. The stiffening spars 62, 64 may have a cross-sectional dimension greater than or equal to approximately 5 mm. The stiffening spars 62, 64 may also be configured with a cross section that varies along the length of the stiffening spar.

Referring to FIG. 5, according to another embodiment, the stiffening members 51 may comprise one of more stiffening wires 72, 74. It should be appreciated that any number of stiffening wires 72, 74 could be disposed in contact with the collimation plates 34. A partial list of acceptable cross sections for the stiffening wires 72, 74 includes generally rectangular, generally circular, generally oval, and shaped like the letter "I", as would typically be found on an I-beam used for construction. The stiffening wires 72, 74 may preferably have a largest cross-sectional dimension of less than approximately 5 mm. The stiffening wires 72, 74 may also be configured with a cross section that varies along the length of the stiffening wire 72, 74.

For all of the previously described embodiments, it should be understood that the stiffening members 51 may be attached to all of the collimation plates 34 or only to a select plurality of the collimation plates 34. Additionally, some embodiments may have the stiffening members directly in contact with the collimation plates 34. In other embodiments, the stiffening members 51 could be in mechanical communication with the collimation plates 34 through a bracket or a mounting piece (not shown).

The stiffening members 51 are configured to decrease the susceptibility of the collimation plates 34 to bending or deflecting. During the acquisition of data, the collimation plates 34 are subjected to a large g-loading due to the centrifugal force caused by the rotation of the rotatable gantry portion 14 (shown in FIG. 1).

In order to be most effective at stiffening the collimation plates 34, the stiffening members 51 should meet certain criteria. The stiffening members 51 are preferably as light as possible since they will be disposed on the rotatable gantry portion 14 (shown in FIG. 1) and subjected to high centrifugal forces. The stiffening members 51 should preferably be made from a material with a low coefficient of thermal expansion because the temperature in the detector assembly 18 (shown in FIG. 1) can vary significantly while scanning the subject 24 (shown in FIG. 1). If a material with too high a coefficient of thermal expansion is chosen, the alignment of the collimation plates 34 will change significantly as a function of temperature. Also, the stiffening members 51 should be relatively x-ray translucent. The term "x-ray translucent" should be defined to include materials that do not significantly block x-ray photons (not shown). Also, in order to keep the collimation plates 34 relatively stationary, the stiffening members 51 should preferably be made from a generally stiff material. A partial list of materials that could be used to form the stiffening members 51 comprises carbon composite, plastic, carbon fiber reinforced plastic, aluminum, and ceramic.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. A computed tomography system comprising:
    a rotatable gantry portion;
    an x-ray source mounted to the rotatable gantry portion; and
    a detector assembly mounted to the rotatable gantry portion and positioned to receive an x-ray beam from the x-ray source, the detector assembly comprising:
        a plurality of x-ray attenuating collimation plates; and
        a stiffening wire attached to one or more of the plurality of x-ray attenuating collimation plates, wherein the stiffening wire comprises a generally x-ray translucent material.

2. The computed tomography system of claim 1, wherein the stiffening wire is attached to a rail.

3. The computed tomography system of claim 1, wherein the stiffening wire is attached to all of the x-ray attenuating collimation plates.

4. The computed tomography system of claim 1, wherein the detector assembly further comprises a second stiffening wire attached to one or more of the plurality of x-ray attenuating collimation plates.

5. A computed tomography system comprising:
    a rotatable gantry portion;
    an x-ray source mounted on the rotatable gantry portion; and a detector assembly mounted on the rotatable gantry portion generally opposite the x-ray source, the detector assembly comprising:
  a plurality of x-ray attenuating collimation plates configured to block a scattered x-ray photon; and
  a carbon composite stiffening wire attached to one or more of the plurality of x-ray attenuating collimation plates.

6. The computed tomography system of claim 5, wherein the carbon composite stiffening wire is attached to all of the x-ray attenuating collimation plates.

7. The computed tomography system of claim 5, wherein the carbon composite stiffening wire is attached to a rail.

* * * * *